United States Patent
Hashimoto et al.

(10) Patent No.: US 11,013,824 B2
(45) Date of Patent: May 25, 2021

(54) ADHESIVE FOR HARD TISSUE BONDING, ADHESIVE KIT FOR HARD TISSUE BONDING, AND BONE CEMENT

(71) Applicants: Chiba Institute of Technology, Chiba (JP); Fukuyamaika Corporation, Chiba (JP)

(72) Inventors: Kazuaki Hashimoto, Yachiyo (JP); Hirobumi Shibata, Tokyo (JP); Syuhei Aida, Koga (JP); Shigeo Fukuyama, Yokohama (JP); Takashi Meguro, Naka (JP); Shinya Tanaka, Tokyo (JP)

(73) Assignees: Chiba Institute of Technology, Chiba (JP); Fukuyamaika Corporation, Chiba (JP)

( * ) Notice: Subject to any disclaimer, the term of this patent is extended or adjusted under 35 U.S.C. 154(b) by 0 days.

(21) Appl. No.: 16/498,068

(22) PCT Filed: Mar. 27, 2018

(86) PCT No.: PCT/JP2018/012292
§ 371 (c)(1),
(2) Date: Sep. 26, 2019

(87) PCT Pub. No.: WO2018/181245
PCT Pub. Date: Oct. 4, 2018

(65) Prior Publication Data
US 2020/0023095 A1    Jan. 23, 2020

(30) Foreign Application Priority Data
Mar. 30, 2017 (JP) ................................ 2017-066795
May 30, 2017 (JP) ............................ JP2017-106998

(51) Int. Cl.
*A61L 24/00* (2006.01)
*A61L 24/02* (2006.01)
*A61L 24/06* (2006.01)

(52) U.S. Cl.
CPC ......... *A61L 24/0084* (2013.01); *A61L 24/001* (2013.01); *A61L 24/02* (2013.01); *A61L 24/06* (2013.01); *A61L 2430/02* (2013.01)

(58) Field of Classification Search
CPC .................................................. A61L 24/0084
See application file for complete search history.

(56) References Cited

U.S. PATENT DOCUMENTS

| | | |
|---|---|---|
| 2006/0276562 A1 | 12/2006 | Park et al. |
| 2007/0123603 A1 | 5/2007 | Shalaby et al. |
| 2008/0220045 A1* | 9/2008 | Shalaby .............. A61L 24/0042 424/423 |

FOREIGN PATENT DOCUMENTS

| | | |
|---|---|---|
| JP | 63-011166 A | 1/1988 |
| JP | 01-186805 A | 7/1989 |

(Continued)

OTHER PUBLICATIONS

International Search Report dated Jul. 3, 2018 in corresponding International Application No. PCT/JP2018/012292 and its English translation.

*Primary Examiner* — Michael F Pepitone
(74) *Attorney, Agent, or Firm* — Jon Gordon; Haug Partners LLP

(57) ABSTRACT

An adhesive for hard tissue bonding which has a sufficient pot life and excellent biocompatibility and is replaced with bone over time, and an adhesive kit for hard tissue bonding are provided. In addition, bone cement is provided which has excellent biocompatibility and is replaced with bone over time. An adhesive for hard tissue bonding includes: a cyanoacrylate monomer; and beta-tricalcium phosphate or (Continued)

hydroxyapatite. An adhesive kit for hard tissue bonding includes: a liquid agent containing a cyanoacrylate monomer; and a powdery agent containing beta-tricalcium phosphate or hydroxyapatite. Bone cement includes: a cyanoacrylate polymer; and beta-tricalcium phosphate or hydroxyapatite.

7 Claims, 7 Drawing Sheets

(56) References Cited

FOREIGN PATENT DOCUMENTS

| | | |
|---|---|---|
| JP | 04-044770 A | 2/1992 |
| JP | 2004-236939 A | 8/2004 |
| JP | 2004-534575 A1 | 11/2004 |
| JP | 2014-036733 A | 2/2014 |
| JP | 2015-173788 A | 10/2015 |
| KR | 10-2016-0028731 A | 3/2016 |
| WO | WO 2008/056516 A1 | 5/2008 |

* cited by examiner

US 11,013,824 B2

ADHESIVE FOR HARD TISSUE BONDING, ADHESIVE KIT FOR HARD TISSUE BONDING, AND BONE CEMENT

TECHNICAL FIELD

The present invention relates to an adhesive for hard tissue bonding, an adhesive kit for hard tissue bonding, and bone cement. The present invention is the National Stage entry under 35 U.S.C. § 371 of International Application No. PCT/JP2018/012292 filed on Mar. 27, 2018, published on Oct. 4, 2018 under Publication Number WO 2018/181245 A1, which priority is claimed on Japanese Patent Application No. 2017-066795, filed on Mar. 30, 2017 and Japanese Patent Application No. 2017-106998, filed on May 30, 2017, the contents of which are incorporated herein by reference.

BACKGROUND ART

In recent years, the estimated number of patients with osteoarthritis and osteoporosis among locomotive syndromes that an aging society has increased year by year to 54.7 million people. Furthermore, the annual number of patients requiring artificial joint replacement is 66,000 cases of gonarthrocace, 47,000 cases of coxarthrosis, and 55,000 cases of femoral prosthesis (refer to Yano Research Institute Ltd., 2015, 6th Scientific Commission Medical Device Expert Committee).

Examples of bone cement with which bones, joints, and the like are filled for treatment of the above-described diseases in the related art include ones (for example, refer to PTL 1) which have a synthetic resin as a main component and contain radiopaque materials such as barium sulfate, tantalum, and tungsten for making bone cement impermeable to X-rays.

On the other hand, a 2-cyanoacrylate adhesive is conventionally known as an instant adhesive and has excellent adhesiveness. In addition, a 2-cyanoacrylate adhesive has been used as an adhesive for bonding soft tissue of the esophagus, the stomach, the intestinal tract, the digestive tract, blood vessels, the trachea, and anastomosis of bronchi (refer to, for example, PTL 2).

CITATION LIST

Patent Literature

[PTL 1] Published Japanese Translation No. 2004-534575 of the PCT International Publication
[PTL 2] PCT International Publication No. WO2008/056516

SUMMARY OF INVENTION

Technical Problem

The bone cement disclosed in PTL 1 has a sufficient pot life. However, it contains a synthetic resin and a radiopaque material and is only fixed to irregularities of the bone surface after bone filling, and therefore, has a composition without bone affinity. For this reason, it has been pointed out that there are many cases where peeling off from the bones due to deterioration over time easily occurs, which requires re-operation. In addition, a tissue disorder due to heat generation (at about 60° C.) at the time of curing of a synthetic resin is a problem.

In addition, the 2-cyanoacrylate adhesive disclosed in PTL 2 has a short pot life and it is difficult to finely adjust the adhesion position after application of the adhesive in a case of being used in hard tissue such as bones or cartilage. Therefore, it is difficult to use it as an adhesive for hard tissue bonding.

The present invention has been made from the viewpoint of the above-described circumstances, and provides an adhesive for hard tissue bonding which has a sufficient pot life and excellent biocompatibility and is replaced with bone over time, and an adhesive kit for hard tissue bonding. In addition, the present invention provides bone cement which has excellent biocompatibility and is replaced with bone over time.

Solution to Problem

The inventors have conducted intensive studies in order to achieve the above-described objects. As a result, they have found that a 2-cyanoacrylate adhesive and an adhesive for hard tissue bonding which contains a bone component such as beta-tricalcium phosphate (hereinafter, β-TCP) or hydroxyapatite have a sufficient pot life and excellent biocompatibility and are replaced with bone over time.

That is, the present invention includes the following aspects.

An adhesive for hard tissue bonding according to a first aspect of the present invention includes: a cyanoacrylate monomer; and β-TCP or hydroxyapatite.

In the β-TCP, a part of a calcium position in a crystal may be replaced with a magnesium ion by dissolution and some vacancies existing in a crystalline structure may be replaced with sodium ions by dissolution.

In the β-TCP, a part of a phosphorus position in a crystal may be replaced with a silicon ion by dissolution.

The adhesive for hard tissue bonding according to the first aspect may include: less than or equal to 5 mol % of the silicon ions with respect to all anion positions.

An average particle diameter of the β-TCP and the hydroxyapatite may be less than or equal to 100 μm.

An average particle diameter of the β-TCP and the hydroxyapatite may be less than or equal to 50 μm.

The β-TCP and the hydroxyapatite may be spherical particles.

An adhesive kit for hard tissue bonding according to a second aspect of the present invention includes: a liquid agent containing a cyanoacrylate monomer; and a powdery agent containing β-TCP or hydroxyapatite.

The adhesive kit for hard tissue bonding according to the second aspect may be for trowel-coating or syringe injection.

Bone cement according to a third aspect of the present invention includes: a cyanoacrylate polymer; and β-TCP or hydroxyapatite.

In the bone cement according to the third aspect, a compressive strength may be greater than or equal to 30 MPa.

In the bone cement according to the third aspect, a compression modulus of elasticity may be less than or equal to 50 GPa.

In the bone cement according to the third aspect, a bending strength may be greater than or equal to 30 MPa.

In the bone cement according to the third aspect, a bending modulus of elasticity may be less than or equal to 80 GPa.

Advantageous Effects of Invention

The adhesive for hard tissue bonding and the adhesive kit for hard tissue bonding of the aspects have a sufficient pot life and excellent biocompatibility. The bone cement of the aspect has excellent biocompatibility and is replaced with bone over time.

DESCRIPTION OF EMBODIMENTS

<<Adhesive for Hard Tissue Bonding>>

Figure 1A:
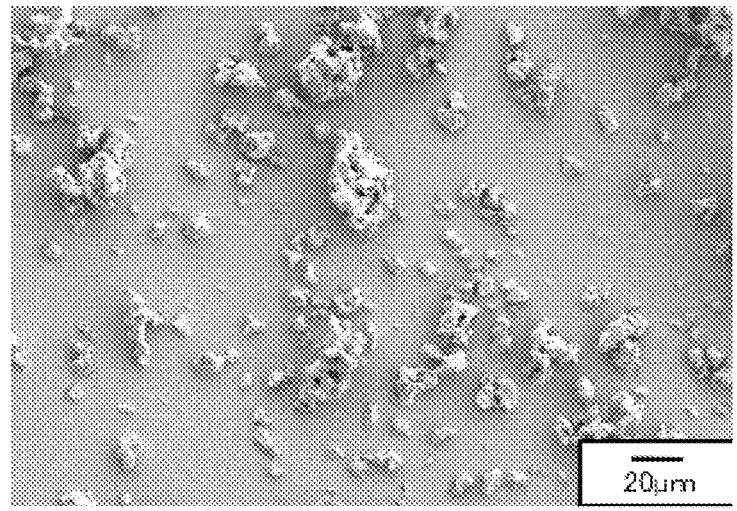
FIG. 1A is a scanning electron microscope (SEM) image of a sample (hereinafter, sometimes referred to as "1 mol % β-TCP/Si") obtained by dissolving 1 mol % silica in β-TCP subjected to non-spray drying treatment in Production Example 1.

An adhesive for hard tissue bonding according to the present embodiment includes: a cyanoacrylate monomer; and β-TCP or hydroxyapatite.

An adhesive for hard tissue bonding in the related art has a synthetic resin as a main component, contains magnesium sulfate or the like in order to impart radiopacity, and is neither biocompatible nor bone resorptive. For this reason, in a lesion part filled with the adhesive for hard tissue bonding in the related art, there have been problems with fixation failure and sharp decrease in bone mass.

On the other hand, since the adhesive for hard tissue bonding of the present embodiment has a sufficient pot life, it is easy to handle it when filling the lesion part. In addition, the component has biocompatibility and is replaced with bone over time in the lesion part filled with a cured body (bone cement) of the adhesive for hard tissue bonding of the present embodiment. For this reason, it is possible to efficiently promote bone regeneration of the filled lesion part.

In the present specification, the "pot life" means the time until a multi-liquid composition in which a combination of a main agent and a curing agent, a combination of a main agent, a curing agent, and a curing promoter, or the like starts to be cured through a reaction. The adhesive for hard tissue bonding of the present embodiment has a pot life of 4 minutes to 60 minutes, preferably 5 minutes to 30 minutes, and more preferably 6 minutes to 20 minutes. In a case where the pot life is within the above-described ranges, in orthopedic surgery of a disease of the bones or joints, it is easy to handle the adhesive since the time until the curing is not too short. Moreover, an increase in surgery time is prevented since the time until curing is not too long, and therefore, the burden on a patient also decreases.

In addition, in the present specification, examples of the "hard tissue" include the bones, the teeth, and nails.

In addition, in the present specification, the "bone resorption" means a phenomenon in which bone and a graft as a substitute thereof are resorbed by an operation of osteoclasts or the like. In addition, "bone formation" means a phenomenon in which new bone is formed in a portion resorbed by an operation of osteoblasts and the like. The "bone resorption" and "bone formation" are also collectively called "bone metabolism" or "bone remodeling". In addition, "bone replacement" means a phenomenon in which a bone and a graft as a substitute thereof are resorbed and replaced with new bone. The cured body (bone cement) of the adhesive for hard tissue bonding of the present embodiment is replaced with bone over time, and therefore, it is inferred that bone is efficiently regenerated in a replaced lesion part.

<Cyanoacrylate Monomer>

A cyanoacrylate monomer having biocompatibility may be used as the cyanoacrylate monomer contained in the adhesive for hard tissue bonding of the present embodiment, and examples thereof include Japanese Examined Patent Application, Second Publication No. S48-10379, PCT International Publication No. WO2002/053666, and PCT International Publication No. WO2008/056516. Specific examples thereof include compounds represented by Formula (1), (2), or (3) (hereinafter, sometimes referred to as a "compound (1)", a "compound (2)", and a "compound (3)".

(1)

(In Formula (1), $R^{11}$ is an alkyl group or an alkoxy group having 1 to 10 carbon atoms.)

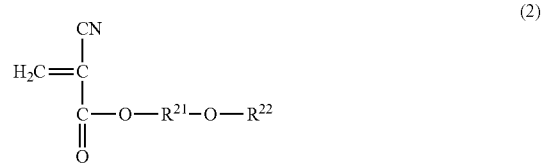

(2)

(In Formula (2), $R^{2'}$ is an alkylene group having 2 to 4 carbon atoms, $R^{22}$ is an alkyl group having 5 to 8 carbon atoms in a case where the number of carbon atoms of $R^{21}$ is 2, and $R^2$ is an alkyl group having 4 to 8 carbon atoms in a case where the number of carbon atoms of $R^{21}$ is 3 or 4.)

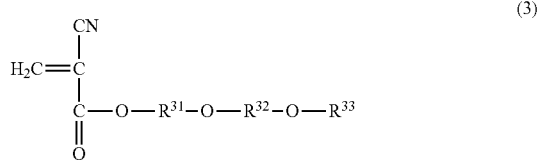

(3)

(In Formula (3), $R^{31}$ and $R^{32}$ are alkylene groups having 2 to 4 carbon atoms, $R^{33}$ is an alkyl group having 4 to 8 carbon atoms in a case where the number of carbon atoms of $R^{31}$ and $R^{32}$ is 2, and $R^{33}$ is an alkyl group having 3 to 8 carbon atoms in a case where the number of carbon atoms of $R^{31}$ and $R^{32}$ is 3 or 4.)

[$R^{11}$]

The alkyl group having 1 to 10 carbon atoms of $R^{11}$ may be linear or branched, and specific examples thereof include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, 1-methylbutyl group, n-hexyl group, 2-methylpentyl group, 3-methylpentyl group, 2,2-dimethylbutyl group, 2,3-dimethylbutyl group, n-heptyl group, 2-methylhexyl group, 3-methylhexyl group, 2,2-dimethylpentyl group, 2,3-dimethylpentyl group, 2,4-dimethylpentyl group, 3,3-dimethylpentyl group, 3-ethylpentyl group, 2,2,3-trimethylbutyl group, n-octyl group, an isooctyl group, a 2-ethylhexyl group, a nonyl group, and a decyl group. Among these, the alkyl group having 1 to 10 carbon atoms of $R^1$ is preferably linear, more preferably a methyl group, an ethyl group, an n-propyl group, or an n-butyl group, and still more preferably an ethyl group or an n-butyl group from the viewpoint that the amount of formaldehyde released is small.

The alkoxy group having 1 to 10 carbon atoms of $R^{11}$ may have a structure in which a linear or branched alkyl group having 1 to 10 carbon atoms binds to an oxygen atom. Specific examples thereof include a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a neopentoxy group, a tert-pentoxy group, 1-methylbutoxy group, an n-hextoxy group, 2-methylpentoxy group, 3-methylpentoxy group, 2,2-dimethylbutoxy group, 2,3-dimethylbutoxy group, n-heptoxy group, 2-methylhextoxy group, 3-methylhextoxy group, 2,2-dimethylpentoxy group, 2,3-dimethylpentoxy group, 2,4-dimethylpentoxy group, 3,3-dimethylpentoxy group, 3-ethylpentoxy group, 2,2,3-trimethylbutoxy group, n-octoxy group, an isooctoxy group, 2-ethylhextoxy group, a nonoxy group, and a disiloxy group. Among these, the alkoxy group having 1 to 10 carbon atoms of $R^{11}$ is preferably linear, more preferably a methoxy group, an ethoxy group, an n-propoxy group, or an n-butoxy group, and still more preferably an ethoxy group or an n-butoxy group from the viewpoint that the amount of formaldehyde released is small.

Among these, $R^{11}$ in the compound (1) is preferably linear, more preferably methyl group, an ethyl group, an n-propyl group, or n-butyl group, a methoxy group, an ethoxy group, an n-propoxy group, or an n-butoxy group, and still more preferably an ethyl group, an n-butyl group, an ethoxy group, or an n-butoxy group from the viewpoint that the amount of formaldehyde released is small.

[$R^{21}$ and $R^{22}$]

The alkylene group having 2 to 4 carbon atoms of $R^{21}$ may be a linear or branched alkylene group. Specific examples thereof include an ethylene group, an n-propylene group, an isopropylene group, an n-butylene group, an isobutylene group, and a sec-butylene group. Among them, the alkylene group having 2 to 4 carbon atoms of $R^{21}$ is preferably linear and more preferably an ethylene group, an n-propylene group, or an isopropylene group.

Examples of the alkyl group having 4 to 8 or 5 to 8 carbon atoms of $R^{22}$ include the same as those exemplified in the above-described $R^{11}$.

Among these, when the number of carbon atoms of $R^{21}$ is 2, the number of carbon atoms of $R^2$ is 5 to 8, preferably 6 to 8, and more preferably 7 to 8. In a case where the number of carbon atoms of $R^{21}$ and $R^{22}$ is within the above-described ranges, the amount of formaldehyde released is appropriate, and a biological adhesive having excellent safety and sufficient degradability can be obtained.

Among these, when the number of carbon atoms of $R^{21}$ is 3, the number of carbon atoms of $R^{22}$ is preferably 4 to 8. In a case where the number of carbon atoms of $R^{21}$ and $R^{22}$ is within the above-described ranges, the amount of formaldehyde released is appropriate, and an adhesive for hard tissue bonding having excellent safety and sufficient degradability can be obtained.

[$R^{31}$, $R^{32}$, and $R^{33}$]

Examples of the alkylene group having 2 to 4 carbon atoms of $R^{31}$ and $R^{32}$ include the same as those exemplified in the above-described $R^{21}$.

Examples of the alkyl group having 4 to 8 or 5 to 8 carbon atoms of $R^{33}$ include the same as those exemplified in the above-described $R^{11}$.

Among these, when the number of carbon atoms of $R^{31}$ and $R^{32}$ is 3, the number of carbon atoms of $R^{33}$ is preferably 3 to 5. In a case where the number of carbon atoms of $R^{31}$, $R^{32}$ and $R^{33}$ is within the above-described ranges, the hardness further decreases, and an adhesive for hard tissue bonding having excellent flexibility can be obtained.

More specific examples of the compound (1) include, but are not limited to, methyl-2-cyanoacrylate, ethyl-2-cyanoacrylate, propyl-2-cyanoacrylate, isopropyl-2-cyanoacrylate, butyl-2-cyanoacrylate, isobutyl-2-cyanoacrylate, amyl-2-cyanoacrylate, hexyl-2-cyanoacrylate, cyclohexyl-2-cyanoacrylate, octyl-2-cyanoacrylate, 2-ethylexyl-2-cyanoacrylate, allyl-2-cyanoacrylate, benzyl-2-cyanoacrylate, methoxyethyl-2-cyanoacrylate, ethoxyethyl-2-cyanoacrylate, methoxypropyl-2-cyanoacrylate, and tetrahydrofurfuryl-2-cyanoacrylate. Among these, ethyl-2-cyanoacrylate or butyl-2-cyanoacrylate is preferable as the compound (1).

More specific examples of the compound (2) include, but are not limited to, 2-hextoxyethyl-2-cyanoacetate, 2-heptoxyethyl-2-cyanoacetate, 2-(2-ethylhextoxy) ethyl-2-cyanoacrylate, 2-butoxyisopropyl-2-cyanoacrylate, 2-hextoxyisopropyl-2-cyanoacrylate, 2-(2-ethylhextoxy) isopropyl-2-cyanoacrylate, and 2-octoxyethyl-2-cyanoacetate.

More specific examples of the compound (3) include, but are not limited to, 2-(2-butoxyethoxy) ethyl-2-cyanoacrylate, 2-(2-propoxyisopropoxy) isopropyl-2-cyanoacrylate, and 2-(2-butoxypropoxy) isopropyl-2-cyanoacrylate.

The adhesive for hard tissue bonding of the present embodiment may contain at least one of the compound (1), the compound (2), or the compound (3) as a cyanoacrylate monomer, or two or more kinds in combination as a cyanoacrylate monomer.

<Method for Producing Cyanoacrylate Monomer>

A method for producing a cyanoacrylate monomer contained in the adhesive for hard tissue bonding of the present embodiment is not particularly limited. For example, cyanoacetic acid ester produced through an esterification reaction of cyanoacetic acid and alcohol may be reacted in the presence of a catalyst in a solvent for condensation. An amine or a base may be used as a catalyst.

Examples of the amine include piperidine, diethylamine, diethylamine, and morpholine.

Examples of the base include salts of potassium hydroxide, sodium hydroxide, sodium alkoxide, and a secondary amine.

A catalyst is used within a range of 0.001 to 10 mol and preferably 0.01 to 1 mol with respect to cyanoacetic acid ester. Toluene, an ethyl acetate, or the like is used as a solvent. The reaction temperature can be set to a temperature at which it is possible to reflux the solvent.

Subsequently, the solvent is distilled off from the condensation liquid, and then, phosphorus pentoxide, phosphoric acid, condensed phosphoric acid, and the like are added to the condensation liquid from which the solvent is distilled off by 0.01 to 10 mass % and preferably 0.5 to 3 mass %, and the mixture is heated at 140° C. to 250° C. and depolymerized. A crude 2-cyanoacrylate compound generated through the depolymerization is distilled, the purity is increased, and 2-cyanoacrylate monomer to be used in the adhesive for hard tissue bonding of the present embodiment can be obtained.

<Artificial Aggregate>

The adhesive for hard tissue bonding of the present embodiment contains β-TCP or hydroxyapatite as an artificial aggregate. The adhesive may contain either both β-TCP or hydroxyapatite or both β-TCP and hydroxyapatite.

In general, three phases of β, α, and α' are present in "tricalcium phosphate" (TCP; $Ca_3(PO_4)_2$) from low temperature. α'-TCP is stable at a high temperature from about 1,450° C. and is not obtained at normal temperature. Although phase transition is performed from α-TCP to β-TCP at 1,120° C. to 1,180° C., α-TCP is present as a metastable phase at normal temperature since the speed of the transition is slow. It is naturally present as whitlockite $(Ca_{18}(Mg,Fe)_2H_2(PO_4)_{14}$, similar to the β phase). Both α-TCP and β-TCP are bioactive materials and are used as bioceramics.

In addition, in general, "hydroxyapatite" (HAp) is a generic term for apatite which mainly contains a hydroxyl group as a monovalent anion. It is a main component of hard tissue such as the bones and the teeth of vertebrates including humans. Commercially available HAp may be used, and examples thereof include, but are not limited to, "hydroxyapatite" manufactured by Taihei Chemical Industrial Co., Ltd. (average particle diameter of 4 to 6 μm), "spherical HAP" (average particle diameter of 15 to 20 μm), and "HAP-200" (average particle diameter of 5 to 20 μm).

[beta-tricalcium phosphate (β-TCP)]

(Crystal Structure of β-TCP)

A space group of β-TCP is R3c and belongs to a rhombohedral system. The lattice constant is a=1.04391 nm, c=3.73756 nm in a hexagonal lattice setting. In addition, as described in well-known literature (Japanese Unexamined Patent Application, First Publication No. 2015-173788), two columns of A and B, which consist of a Ca polyhedron and a $PO_4$ tetrahedron in a crystalline structure (unit lattice) of β-TCP and are crystallographically independent, are present parallel to a c-axis.

A column A is present on the c-axis (threefold axis), and is a repetition of p(1)-Ca(4)-Ca(5)-P(1)-vacancy(o)-Ca(5)-P(1). In the natural mineral whitlockite, other metal ions such as Mg or Fe are substituted at the Ca(4) and Ca(5) positions. In addition, since the space occupancy rate of the Ca(4) position is about 0.5, it is a unique crystalline structure in which there is a vacancy in the column A.

A column B is a repetition of P(2)-P(3)-Ca(1)-Ca(3)-Ca(2)-P(2)-P(3), but three Ca's form a broken line without being on a straight line.

(Replacement with Cation by Dissolution)

In β-TCP used in the adhesive for hard tissue bonding of the present embodiment, a part of a calcium position in a crystal may be replaced with a magnesium ($Mg^{2+}$) ion by dissolution as a divalent cation, or vacancies existing in a crystalline structure may be replaced with sodium ($Na^+$) ions by dissolution as monovalent cations.

In general, a "magnesium ion" activates the most important enzyme ATPase, which is an energy source in a cell. A magnesium ion binds to ATP as a substrate, and ATPase acts on this complex to produce energy.

In addition, in general, a "sodium ion", as a monovalent cation, is closely related to an important function in vivo along with a hydrogen ion. Specifically, the sodium ion is required in the process of cell adhesion with apatite in vivo, bone metabolism, or bone resorption.

In the present embodiment, β-TCP preferably contains calcium ions in an amount less than or equal to 100 mol % and particularly preferably 86.3 mol % to 95.5 mol %, with respect to all cation positions.

In addition, in the present embodiment, β-TCP preferably contains magnesium ions in an amount greater than or equal to 0 mol % and less than 10.0 mol/o and particularly preferably about 9.1 mol %, with respect to all cation positions.

In addition, in the present embodiment, β-TCP preferably contains sodium ions in an amount of 0 mol % to 2.0 mol %, with respect to all cation positions. The content (mol %) of each ion can be calculated using Formula (A).

In Formula (A), the ion X is a calcium ion, a magnesium ion, or a sodium ion.

$$\text{(Content of specific ion } X(\text{mol \%}))=X[\text{mol}]/(Ca+Mg+Na+\text{vacancy}(o))[\text{mol}]\times 100 \quad (A)$$

(Replacement with Anion by Dissolution)

In β-TCP of the present embodiment, a phosphorus position in a crystal may be replaced with a silicon ion by dissolution.

In general, the "silicon ion" forms a cross-linking structure with polysaccharides through binding such as R'—O—Si—O—R" or with acidic mucopolysaccharides such as hyaluronic acid sulfate or chondroitin sulfate to impart strength or elasticity to connective tissue. Such a cross-linking structure of silicon stabilizes the skin chemically and mechanically, maintains the permeability or elasticity of the blood vessel wall, and expresses a normal function. It is known that there are 3 to 6 silicons per α-protein chain in a collagen molecule which is a main protein that constitutes connective tissue. Accordingly, the lack of silicon causes damage to bone tissue or connective tissue. In addition, the content of silicon of the aorta, the thymus, the skin, and the like decreases as humans age, and accordingly, the incidence of arteriosclerosis increases. It is known that silicon has an action of inhibiting lipid deposition and preventing arteriosclerosis. In addition, a surface charge in an inorganic material containing silicon exhibits a negative charge, and an effect due to the negative charge promotes adsorption or the like of the extracellular matrix. Furthermore, the presence of silicic acid on the surface of the material can promote formation of bone-like apatite and can enhance the adhesiveness between the material and bone of a living body and formation of new bone.

In the present embodiment, β-TCP preferably contains phosphorus ions in an amount of 95 mol % to 100 mol % and more preferably 97 mol % to 100 mol %, with respect to all anion positions.

In addition, in the present embodiment, β-TCP preferably contains silicon ions in an amount of 0 mol % to 5 mol % and more preferably 1 mol % to 3 mol %, with respect to all anion positions.

The content (mol %) of each ion can be calculated using Formula (B). In Formula (B), the ion Y is a phosphorus ion or a silicon ion.

$$\text{(Content of specific ion Y(mol \%))} = Y[\text{mol}]/(P+Si)[\text{mol}] \times 100 \quad (B)$$

(Molar Ratio of Cation with Respect to Anion)

In the present embodiment, the molar ratio of cations to anions of β-TCP ((Ca+Mg+Na+vacancy)/(P+Si)) is about 1.571.

The molar ratio of cations to anions of HAp (Ca/P) is about 1.677.

Because β-TCP has a lower molar ratio of cation to anion than HAp, the speed of dissolution and resorption in a living body is higher than those of other calcium phosphate ceramics. Therefore, generation of new bone and replacement with autologous bone is performed faster. For this reason, β-TCP is more suitable for clinical application as an artificial dental root or bone filler.

[Average Particle Diameter]

In the present embodiment, the average particle diameter of β-TCP or hydroxyapatite is preferably less than or equal to 100 μm, more preferably less than or equal to 50 μm, still more preferably 1 μm to 50 μm, and still more preferably 10 μm to 50 μm from the viewpoint of high dispersibility without aggregation when β-TCP or hydroxyapatite is mixed with a cyanoacrylate monomer.

As a method for measuring an average particle diameter, it is possible to measure the average particle diameter thereof using, for example, a laser diffraction-scattering type particle size analyzer.

[Particle Shape]

In the present embodiment, the particle shape of β-TCP or HAp is not particularly limited, but examples thereof include: a spherical shape; a spheroid shape; a geometrical shape such as a polyhedron shape, a polygonal pyramid shape, a cone shape, a cylindrical shape, or a frustum shape; and an irregular shape. Among these, the particle shape of β-TCP or hydroxyapatite is preferably spherical.

<Method for Producing Artificial Aggregate>

In the present embodiment, powder particles of β-TCP or HAp may be produced using a known method (for example, Japanese Unexamined Patent Application, First Publication No. 2015-173788).

Specifically, first, wet-mixing of powder raw materials is performed for 48 hours using an alumina ball mill with an ethanol solvent. Ammonium hydrogen phosphate may be used as a phosphorus source and calcium carbonate may be used as a calcium source. At this time, in a case of producing β-TCP in which a calcium position, a vacancy, and a phosphorus position are respectively replaced with a magnesium ion by dissolution, a sodium ion, and a silicon ion, magnesium oxide may be used as a magnesium source, sodium nitrate may be used as a sodium source, and silicon dioxide may be used as a silicon source. These powder raw materials are mixed with each other so as to obtain the above-described content (first mixing step).

Subsequently, the ethanol of the mixed sample is removed using a rotary evaporator and calcined for about 12 hours under the conditions of a calcination temperature of about 900° C. to 1,180° C. and in an air atmosphere (calcination step). Subsequently, the calcined body after the calcination step is dry-mixed for 1 hour using an agate mortar or the like (second mixing step).

In order to obtain particles of β-TCP or HAp with a desired shape such as a sphere, the calcined body may be further molded into a desired shape such as a sphere through a wet method, a dry method, or the like (molding step). The wet method is a method of using adhesion of water or a binder (binding agent) for granulation, and specific examples thereof include a tumbling granulation method, a spray-drying granulation method (spray-drying method), and an extrusion granulation method. In addition, the dry method is a granulation method performed by increasing a cohesive force of a material without using water or a binder (binding agent), and a specific example thereof includes a compression granulation method in which powder is compressed by pressure of a roll or the like. Among these, in the present embodiment, a wet method is preferable, and a spray-drying granulation method (spray-drying method) is more preferable from the viewpoints of obtaining spherical particles and easily controlling the average particle diameter.

Subsequently, the particles after the second mixing step or after the molding step are further calcined for about 12 hours under the conditions of a calcination temperature of about 900° C. to 1,180° C. and in an air atmosphere (calcination step). The obtained calcined body may be used as a powdery agent containing β-TCP or HAp to be shown below.

<Other Components>

The adhesive for hard tissue bonding of the present embodiment may further contain a stabilizer, a thickener, a curing promoter, and the like. In a case where the content of a liquid agent containing a cyanoacrylate monomer in the adhesive for hard tissue bonding is set to 100 mass %, the total content of the other components is preferably less than or equal to 20 mass %, more preferably less than or equal to 10 mass %, and still more preferably less than or equal to 5 mass %.

Examples of the stabilizer include anionic polymerization inhibitors such as sulfur dioxide, para-toluenesulfonic acid, methanesulfonic acid, propane sultone, and boron trifluoride complex and radical polymerization inhibitors such as hydroquinone, catechol, a pyrogallol, butylated hydroxyanisole, and 2,2-methylenebis-(4-methyl-6-t-butylphenol). In a case where the content of a cyanoacrylate monomer is set to 100 parts by mass, as the content of the stabilizer, 1 to 200 mass ppm, particularly 10 to 100 mass ppm of the anionic polymerization inhibitor can be formulated. In addition, 100 to 10,000 mass ppm, particularly 500 to 5,000 mass ppm of the radical polymerization inhibitor can be formulated. These stabilizers may be used alone or in combination of two or more thereof.

Examples of the thickener include an acrylic polymer or copolymer such as poly(meth)acrylate (for example, polymethyl methacrylate), a cellulose derivative such as acetyl cellulose, and acrylic rubber. In a case where the content of a cyanoacrylate monomer is set to 100 parts by mass, as the content of the thickener, 1 to 20 parts by mass, particularly 2 to 10 parts by mass of the thickener can be formulated. These thickeners may be used alone or in combination of two or more thereof.

Examples of the curing promoter include polyethylene glycol derivatives, crown ether derivatives, and calixarene. These curing promoters can be blended at a mass ratio within a range that does not affect storage stability. These curing promoters may be used alone or in combination of two or more thereof.

<<Method for Producing Adhesive for Hard Tissue Bonding>>

The adhesive for hard tissue bonding of the present embodiment is prepared such that the above-described liquid agent containing a cyanoacrylate monomer (and other components as necessary) and the above-described powdery agent of an artificial aggregate are each subjected to sterilization treatment through various methods, and are then mixed with each other. The adhesive for hard tissue bonding of the present embodiment is used for various applications. The method for the sterilization treatment is not particularly limited, and examples thereof include an electron beam sterilization method, a γ-ray sterilization method, a filtration sterilization method, and a dry heat sterilization method. One of these methods may be performed for the sterilization treatment, or two or more methods may be performed for the sterilization treatment as necessary. For example, in a case where a container for the adhesive for hard tissue bonding is a glass ampoule, the adhesive encapsulated in the glass ampoule is dry heat-sterilized or filter-sterilized to aseptically fill the glass ampoule. In a case where the container for the adhesive for hard tissue bonding is made of polyolefin, the adhesive is filter-sterilized to aseptically fill the container. The outside of the containers can be sterilized through ethylene oxide gas sterilization. In addition, sterilization can also be performed through electron beam sterilization or γ-ray sterilization instead of ethylene oxide gas sterilization.

<<Method of Using Adhesive for Hard Tissue Bonding>>

The adhesive for hard tissue bonding of the present embodiment is obtained by mixing the above-described liquid agent containing cyanoacrylate monomer (and other components as necessary) and the above-described powdery agent of an artificial aggregate, and is used for joining hard tissue portions such as the bones, the teeth, and nails to each other or for being grafted on a defective portion of hard tissue as bone cement which is a cured body of an adhesive for hard tissue bonding.

<<Adhesive Kit for Hard Tissue Bonding>>

An adhesive kit for hard tissue bonding according to the present embodiment includes: a liquid agent containing a cyanoacrylate monomer; and a powdery agent containing β-TCP or hydroxyapatite.

The adhesive kit for hard tissue bonding of the present embodiment has a sufficient pot life. For this reason, in a case where an adhesive for hard tissue bonding was prepared beforehand by mixing a liquid agent with a powdery agent in orthopedic treatment of a disease in the bones, the teeth, and the like, it is easy to handle the adhesive when a lesion part is filled therewith. In addition, the component of the adhesive kit for hard tissue bonding has biocompatibility and the cured body (bone cement) of the adhesive for hard tissue bonding is replaced with bone over time. For this reason, it is possible to efficiently promote bone regeneration of the filled lesion part.

<Liquid Agent>

A liquid agent included in the adhesive kit for hard tissue bonding of the present embodiment contains a cyanoacrylate monomer.

Examples of the cyanoacrylate monomer include the same as those exemplified in the above-described adhesive for hard tissue bonding.

Among these, ethyl-2-cyanoacrylate or butyl-2-cyanoacrylate is preferable as the cyanoacrylate monomer.

In the present embodiment, the liquid agent may further contain a stabilizer, a thickener, a curing promoter, and the like. In a case where the content of the liquid agent is set to 100 mass %, the total content of the other components is preferably less than or equal to 20 mass %, more preferably less than or equal to 10 mass %, and still more preferably less than or equal to 5 mass %. Examples of the stabilizer, the thickener, and the curing promoter include the same as those exemplified in the above-described other components.

<Powdery Agent>

A powdery agent included in the adhesive kit for hard tissue bonding of the present embodiment contains β-TCP or HAp. The powdery agent may contain either β-TCP or HAp, or both β-TCP and HAp.

Examples of β-TCP and HAp include the same as those exemplified in the above-described adhesive for hard tissue bonding.

In β-TCP in the present embodiment, a part of a calcium position may be replaced with a magnesium ($Mg^{2+}$) ion by dissolution as a divalent cation, or vacancies may be replaced with sodium ($Na^+$) ions by dissolution as monovalent cations.

In β-TCP of the present embodiment, a phosphorus position in a crystal may be replaced with a silicon ion by dissolution.

Examples of the content of each ion include the same as those exemplified in the above-described adhesive for hard tissue bonding.

In the present embodiment, the average particle diameter of β-TCP or HAp is preferably less than or equal to 100 μm, more preferably less than or equal to 50 μm, still more preferably 1 μm to 50 μm, and still more preferably 10 μm to 50 μm from the viewpoint of high dispersibility without aggregation when β-TCP or hydroxyapatite is mixed with a cyanoacrylate monomer.

In addition, in the present embodiment, examples of the particle shape of β-TCP or HAp include the same as those exemplified in the above-described adhesive for hard tissue bonding. Among these, the particle shape of β-TCP or HAp in the present embodiment is preferably spherical.

<<Method of Using Adhesive Kit for Hard Tissue Bonding>>

As a method of using the adhesive kit for hard tissue bonding of the present embodiment, the above-described liquid agent may be mixed with the above-described powdery agent. The mixing may be performed using, for example, a trowel or a syringe as shown in examples to be described below.

As the mixing ratio (mass ratio), the mass ratio of (β-TCP or HAp in the powdery agent to a cyanoacrylate monomer in a liquid agent is preferably 1:1.3 to 3:1, more preferably 1:1.3 to 2.7:1, and still more preferably 1:1.3 to 1.6:1.

As the application, the adhesive kit may be used for trowel-coating in which a lesion part of hard tissue such as the bones or the teeth are directly coated, or may be used for syringe injection in which the adhesive kit is injected into a lesion part.

<<Bone Cement>>

Bone cement according to the present embodiment includes: a cyanoacrylate polymer, and β-TCP or hydroxyapatite.

The bone cement of the present embodiment has excellent biocompatibility and is replaced with bone over time in a lesion part filled with the bone cement. For this reason, generation of bone is efficiently encouraged in an in vivo graft of the bone cement of the present embodiment.

The above-described polymer or copolymer of the cyanoacrylate polymer is used as the cyanoacrylate polymer contained in the bone cement of the present embodiment. Specific examples thereof include a compound having a structure represented by Formula (4), (5), or (6).

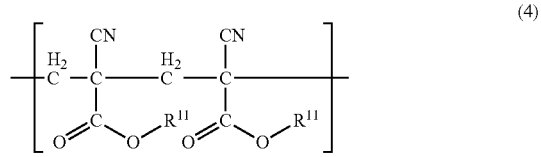

(4)

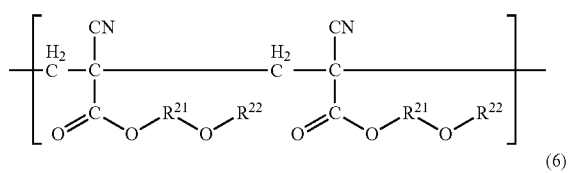

(5)

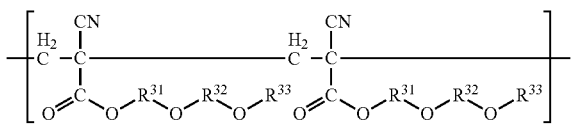

(6)

(In the formulae, $R^{11}$, $R^{21}$, $R^{22}$, $R^{31}$, $R^{32}$, and $R^{33}$ are the same as above.)

The above-described cyanoacrylate monomer reacts with water in the air, and the polymerization reaction proceeds to perform curing. At this time, bone cement is formed by mixing the above-described β-TCP or HAp powder with the cyanoacrylate monomer and dispersing the powder in the cyanoacrylate monomer for curing.

The bone cement of the present embodiment is preferable because it is hardly damaged when the compressive strength increases, thereby having high hardness. Specifically, the compressive strength is greater than or equal to 30 MPa, preferably greater than or equal to 30 MPa and less than 100 MPa, and more preferably 30 MPa to 60 MPa. In a case where the compressive strength is within the above-described ranges, the bone cement has moderate hardness.

On the other hand, the compression modulus of elasticity of the bone cement of the present embodiment is preferably close to that of hard tissue to be joined. Specifically, the compression modulus of elasticity is less than or equal to 50 GPa, preferably 5 GPa to 50 GPa, and more preferably 10 GPa to 48 GPa. In a case where the compression modulus of elasticity is within the above-described ranges, the compression modulus of elasticity is close to that of hard tissue to be joined and the bone cement has moderate elasticity.

The compressive strength and the compression modulus of elasticity can be measured, for example, through the following method.

First, a cylindrical test sample (for example, 14 mm diameter×15 mm height) is prepared for bone cement. Subsequently, the test sample is subjected to a compressive strength test using a compression tester (for example, Autograph AG-1 (manufactured by Shimadzu Corporation)) to measure the compression breaking load and the compressive elastic force. Subsequently, the compressive strength can be calculated by dividing the obtained compression breaking load by the cross-sectional area of the test sample. In addition, the compression modulus of elasticity can be calculated by dividing the compressive elastic force by the cross-sectional area of the test sample.

In addition, the bone cement of the present embodiment is preferable because it is hardly damaged when the bending strength increases, thereby having high hardness. Specifically, the bending strength is greater than or equal to 30 MPa, preferably greater than or equal to 30 MPa and less than 100 MPa, and more preferably 40 MPa to 60 MPa. In a case where the bending strength is within the above-described ranges, the bone cement has moderate hardness.

On the other hand, the bending modulus of elasticity of the bone cement of the present embodiment is preferably close to that of hard tissue to be joined. Specifically, the bending modulus of elasticity is greater than or equal to 80 GPa, preferably 5 GPa to 79 GPa, and more preferably 10 GPa to 79 GPa. In a case where the bending modulus of elasticity is within the above-described ranges, the bending modulus of elasticity is close to that of hard tissue to be joined and the bone cement has moderate elasticity.

The bending strength and the bending modulus of elasticity can be measured, for example, through the following method.

First, a prism-like test sample (for example, 3 mm long×4 mm wide×30 mm height) is prepared for bone cement. Subsequently, the test sample is subjected to a three-point bending strength test using a bending tester (for example, Autograph AG-1 (manufactured by Shimadzu Corporation)) to measure the maximum load (Pmax) and the bending elasticity (Δ) until breakage.

Subsequently, the bending strength can be calculated using the obtained maximum load (Pmax) until breakage and Equation (C). In Equation (C), h represents a longitudinal length of the test sample, Pmax represents a test force, l represents a distance between supporting points (that is, a height of the test sample), and b represents a lateral length of the test sample.

$$\text{Bending Strength }(\delta)=M/I\times h/2=(3\times P\max \times l)/(2\times b\times h) \quad (C)$$

In addition, the bending modulus of elasticity can be calculated using the obtained bending elasticity and Equation (D). In Equation (D), Δ represents bending elasticity, and l, b and h are the same as those in Equation (C).

$$\text{Bending modulus of elasticity }(E)=(\Delta\times l^3)/(4\times b\times h^3) \quad (D)$$

The bone cement of the present embodiment can be used for joining hard tissue portions such as the bones, the teeth, and nails to each other or for being grafted on a defective portion of hard tissue. Accordingly, the bone cement of the present embodiment is useful for treating diseases associated with hard tissue (for example, osteoarthritis and osteoporosis).

EXAMPLES

Hereinafter, the present invention will be described using examples, but is not limited to the following examples.

Production Example 1 Production of Artificial Aggregate (1) Production of (β-TCP Powder and β-TCP/Si Powder β-TCP and a substance obtained by dissolving a trace amount of metal silica in β-TCP (hereinafter, sometimes referred to as "β-TCP/Si") were produced through a well-known method (reference: Japanese Unexamined Patent Application, First Publication No. 2015-173788).

Specifically, first, ammonium hydrogen phosphate, calcium carbonate, magnesium nitrate, magnesium oxide, and silicon dioxide were placed in an alumina ball such that each final ion composition became a composition shown in Table 1, ethanol was added thereto as a solvent, and the mixture was wet-mixed. The pulverization time was 48 hours. Subsequently, ethanol was removed using a rotary evaporator.

Subsequently, the mixture was calcined at a calcination temperature of 900° C. for 12 hours in an air atmosphere. Subsequently, the mixture was dry-mixed for 1 hour using an agate mortar. Subsequently, the mixture was calcined at a calcination temperature of 900° C. for 12 hours in an air atmosphere to produce β-TCP powder before spray-drying treatment (non-spray drying treatment) or powder obtained by dissolving a trace amount of metal silica in β-TCP (hereinafter, sometimes referred to as "β-TCP/Si").

(2) Spray-Drying Treatment Step

Subsequently, each part of the β-TCP powder and the (β-TCP/Si powder obtained in (1), commercially available β-TCP powder (manufactured by Taihei Chemical Industrial Co., Ltd.) (hereinafter, sometimes referred to as "β-TCP100"), and hydroxyapatite powder (hereinafter, sometimes referred to as "HAp") (of which the particle shape is spherical and which is manufactured by Taihei Chemical Industrial Co., Ltd.) was suspended in a binder-added aqueous solution (a 5% to 20% PVA aqueous solution in which polyvinyl alcohol (PVA) is used as a binder) to make powder through spray-drying (hereinafter, sometimes referred to as "SP").

(3) Calcination Step

Subsequently, each non-SP-treated β-TCP and (β-TCP/Si obtained in (1), commercially available (β-TCP100, commercially available HAp, and β-TCP, β-TCP/Si, β-TCP100, and HAp, which were subjected to SP treatment and obtained in (2), was sintered at 1,130° C. to obtain insoluble fine particles. The average particle diameter of the non-SP-treated and sintered particles was about 2 to 80 μm. On the other hand, the average particle diameter of the sintered particles after the SP treatment was about 10 to 50 μm.

Figure 1B:
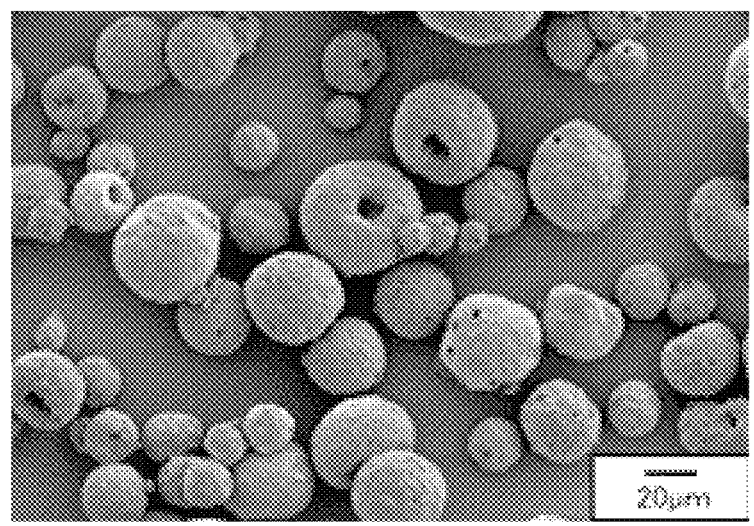
FIG. 1B is an SEM image of 1 mol % β-TCP/Si sintered at 1,130° C. after spray drying (hereinafter, sometimes referred to as "SP") treatment in Production Example 1.

In addition, a scanning electron microscope (SEM) image of a sample (hereinafter, sometimes referred to as "1 mol % β-TCP/Si") obtained by dissolving 1 mol % silica in β-TCP which was not SP-treated and sintered at 1,130° C. is shown in FIG. 1A. An SEM image of 1 mol % β-TCP/Si sintered at 1,130° C. after SP treatment is shown in FIG. 1B.

TABLE 1

| No. | Kind | Anion*[1] | | Cation*[2] | | | | SP treatment | Calcination treatment |
| | | P ion [mol %] | Si ion [mol %] | Ca ion [mol %] | Mg ion [mol %] | Na ion [mol %] | Vacancy [mol %] | | |
| --- | --- | --- | --- | --- | --- | --- | --- | --- | --- |
| 1 | β-TCP | 100 | 0 | 95.45 | 0.00 | 0.00 | 4.55 | None | None |
| 2 | | 100 | 0 | 95.45 | 0.00 | 0.00 | 4.55 | None | Done |
| 3 | | 100 | 0 | 95.45 | 0.00 | 0.00 | 4.55 | Done | Done |
| 4 | β-TCP*[3] | 100 | 0 | 95.45 | 0.00 | 0.00 | 4.55 | None | None |
| 5 | | 100 | 0 | 95.45 | 0.00 | 0.00 | 4.55 | None | Done |
| 6 | | 100 | 0 | 95.45 | 0.00 | 0.00 | 4.55 | Done | Done |
| 7 | | 100 | 0 | 86.35 | 9.10 | 0.00 | 4.55 | None | None |
| 8 | | 100 | 0 | 86.35 | 9.10 | 0.00 | 4.55 | None | Done |
| 9 | | 100 | 0 | 86.35 | 9.10 | 0.00 | 4.55 | Done | Done |
| 10 | β-TCP/Si | 99 | 1 | 86.35 | 9.10 | 0.64 | 3.91 | None | None |
| 11 | | 99 | 1 | 86.35 | 9.10 | 0.64 | 3.91 | None | Done |
| 12 | | 99 | 1 | 86.35 | 9.10 | 0.64 | 3.91 | Done | Done |
| 13 | | 98 | 2 | 86.35 | 9.10 | 1.28 | 3.27 | None | None |
| 14 | | 98 | 2 | 86.35 | 9.10 | 1.28 | 3.27 | None | Done |
| 15 | | 98 | 2 | 86.35 | 9.10 | 1.28 | 3.27 | Done | Done |
| 16 | | 97 | 3 | 86.35 | 9.10 | 1.92 | 2.63 | None | None |
| 17 | | 97 | 3 | 86.35 | 9.10 | 1.92 | 2.63 | None | Done |
| 18 | | 97 | 3 | 86.35 | 9.10 | 1.92 | 2.63 | Done | Done |
| 19 | HAp*[4] | 100 | 0 | 100.00 | 0.00 | 0.00 | 0.00 | None | None |
| 20 | | 100 | 0 | 100.00 | 0.00 | 0.00 | 0.00 | None | Done |
| 21 | | 100 | 0 | 100.00 | 0.00 | 0.00 | 0.00 | Done | Done |

*[1]Anion (Y) [mol %] = Y/(P + Si) × 100 Y = P or Si
*[2]Cation (X) [mol %] = X/(Ca + Mg + Na + vacancy) × 100 X = Ca, Mg or Na
*[3]In case of β-TCP, (Ca + Mg + Na + vacancy)/(P + Si) molar ratio = 1.5710
*[4]In case of HAp, Ca/P molar ratio = 1.677

Although the average particle diameter varied in the non-SP-treated and sintered samples, the particle diameter in the SP-treated and sintered samples was within a constant range and the particle diameters were uniform.

In addition, from FIGS. 1A and 1B, the particle shape of 1 mol % β-TCP/Si which was non-SP-treated and sintered at 1,130° C. was amorphous. In contrast, the particle shape of 1 mol % β-TCP/Si sintered at 1,130° C. after the SP treatment was spherical.

Test Example 1 Mixing Test Using Syringe (1) Measurement of Curing Time

Figure 2:
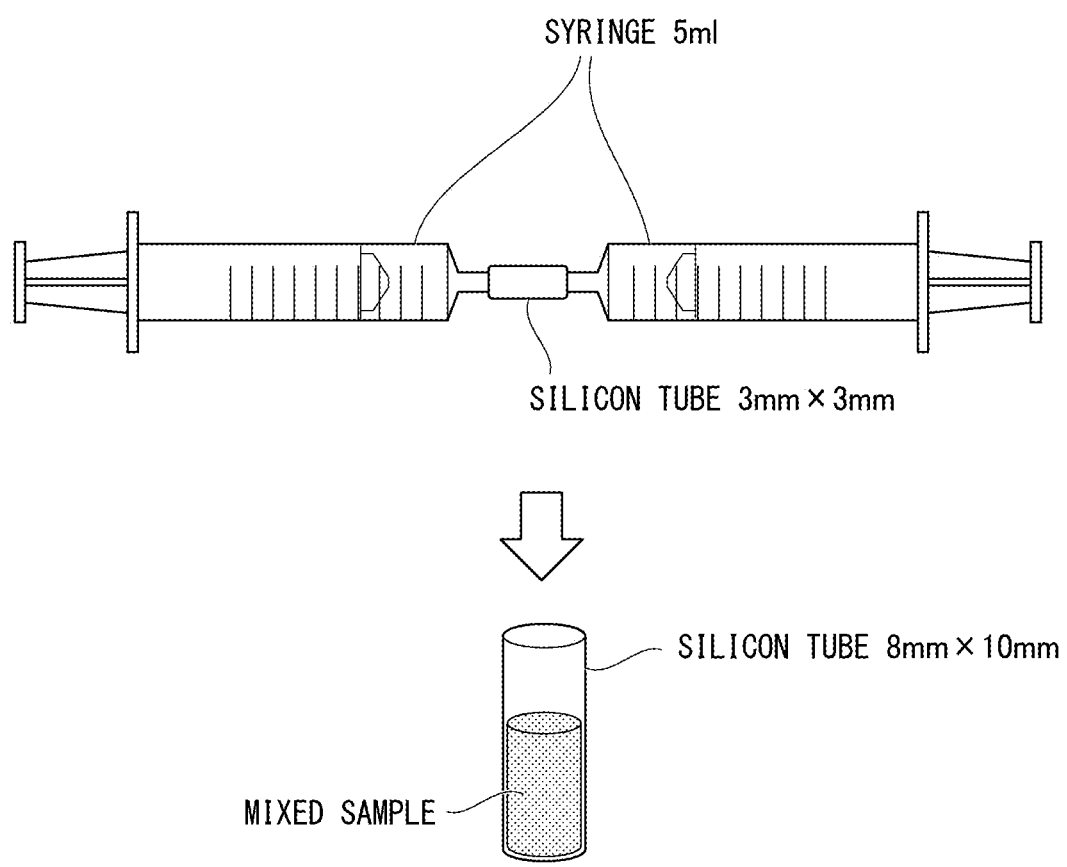
FIG. 2 is a schematic view showing a kneader using a syringe and a silicon tube filled with a mixed sample in Test Example 1.

Subsequently, tests of mixing with a cyanoacrylate adhesive were performed using Nos. 9, 12, and 15 among the artificial aggregates produced in Production Example 1. Specifically, an artificial aggregate was placed in one syringe using a kneader obtained by connecting two 5 mL resin syringes shown in FIG. 2 to each other with a silicon tube (3 mm inner diameter×3 mm long) and a cyanoacrylate adhesive (ARON ALPHA (registered trademark) A "Sankyo", Manufacturer and Distributor: TOAGOSEI CO., LTD., Distributor: Daiichi Sankyo, Inc.) was placed in the other syringe. These were mixed with each other so as to have a mass ratio shown in Table 2. The artificial aggregate was dried for 24 hours at 110° C. before use. Subsequently, the mixed sample was poured into the silicon tube (8 mm inner diameter×10 mm height) shown in FIG. 2. A needle was inserted into the silicon tube every 5 minutes after the pouring. It was determined that the mixture was cured at a point in time when the needle did not pass through the surface of the silicon tube, and the curing time was measured. The results are shown in Table 2. "x" in Table 2 indicates that it was impossible to mix an artificial aggregate with a cyanoacrylate adhesive since these were cured immediately after mixing. The time shown indicates a curing time.

TABLE 2

| | Mass ratio (artificial aggregate [g]: cyanoacrylate adhesive [g]) | | | | | | |
|---|---|---|---|---|---|---|---|
| No. | 1:1.3 | 1:1.2 | 1:1.1 | 1:1 | 1:0.9 | 1:0.8 | 1:0.7 |
| 9 | 30 min | 20 min | x | x | x | x | x |
| 12 | 40 min | 25 min | x | x | x | x | x |
| 15 | 25 min | 20 min | 15 min | 10 min | x | x | x |

From Table 2, in a case where the mass ratio of an artificial aggregate in cases of No. 9 (0 mol % β-TCP/Si which had been subjected to SP treatment and sintered) and No. 12 (1 mol % β-TCP/Si which had been subjected to SP treatment and sintered) to a cyanoacrylate adhesive was 1:1.3 and 1:1.2, the artificial aggregate and the cyanoacrylate adhesive can be mixed with each other. In addition, in a case where the mass ratio of an artificial aggregate No. 15 (2 mol % β-TCP/Si which had been subjected to SP treatment and sintered) to a cyanoacrylate adhesive was 1:1.3 and 1:1.2, 1:1.1, and 1:1, the artificial aggregate and the cyanoacrylate adhesive can be mixed with each other.

From the above, it was confirmed that it is possible to use a mixture of an artificial aggregate having a specific shape and composition, and a cyanoacrylate adhesive at a specific ratio as a bone adhesive having a pot life of 10 minutes to 40 minutes in the kneading using a syringe.

(2) Compressive Strength Test

Subsequently, each cured body obtained after the mixing test in (1) was polished with waterproof abrasive paper (#1500) to prepare a test sample. The obtained test sample was subjected to a compressive strength test using Autograph AG-1 (manufactured by Shimadzu Corporation)) to measure the compression breaking load. Subsequently, the compressive strength was calculated by dividing the obtained compression breaking load by the cross-sectional area of the test sample. The results are shown in Table 3.

TABLE 3

| | Mass ratio (artificial aggregate [g]:cyanoacrylate adhesive [g]) | | | |
|---|---|---|---|---|
| No. | 1:1 | 1:1.1 | 1:1.2 | 1:1.3 |
| 9 | — | — | 46.1 MPa | 36.2 MPa |
| 12 | — | — | 45.8 MPa | 37.2 MPa |
| 15 | 56.6 MPa | 40.0 MPa | 35.7 MPa | 34.6 MPa |

From Table 3, the compressive strength of the obtained cured body was about 30 MPa to 60 MPa.

(3) Observation Using SEM

Figure 3:
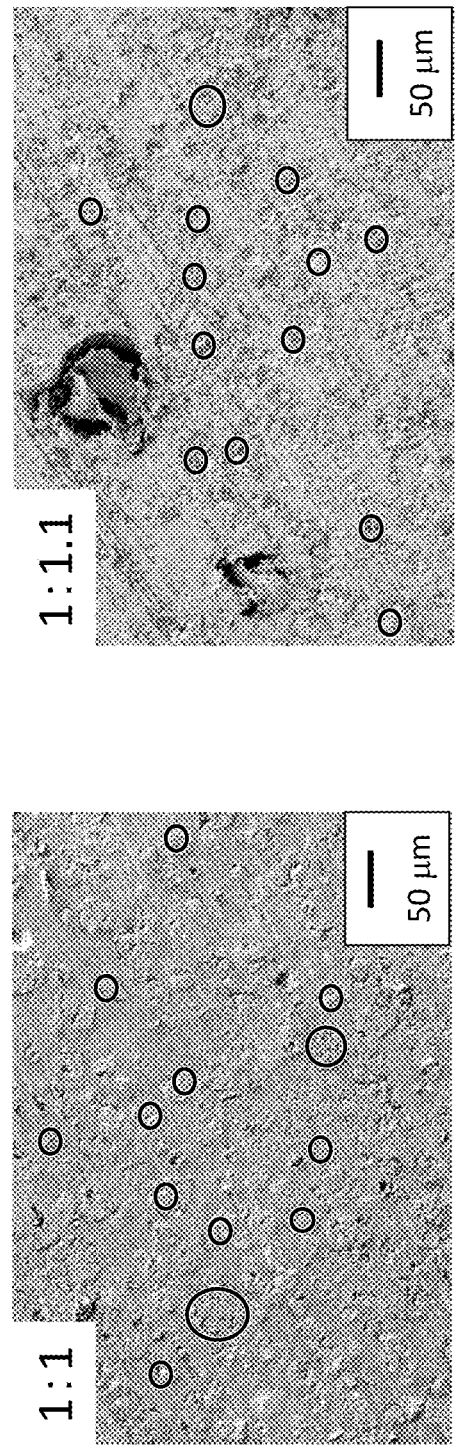
FIG. 3 shows SEM images of cured bodies of which a mass ratio of each artificial aggregate (2 mol % β-TCP/Si which had been subjected to SP treatment and sintered) obtained from a kneading test using the syringe in Test Example 1 to a cyanoacrylate adhesive was 1:1, 1:1.1, 1:1.2, and 1:1.3.
Figure 3:
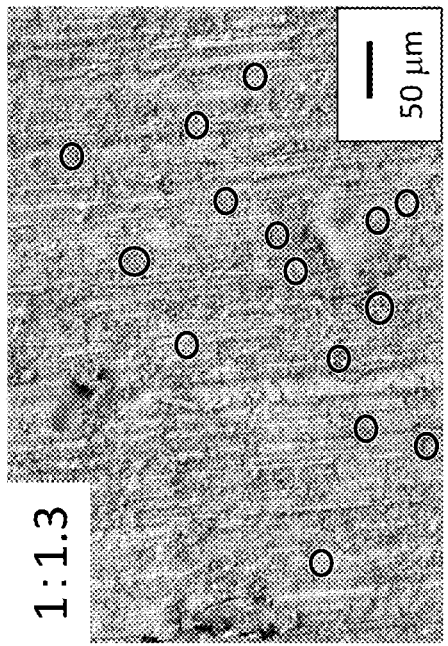
Figure 3:
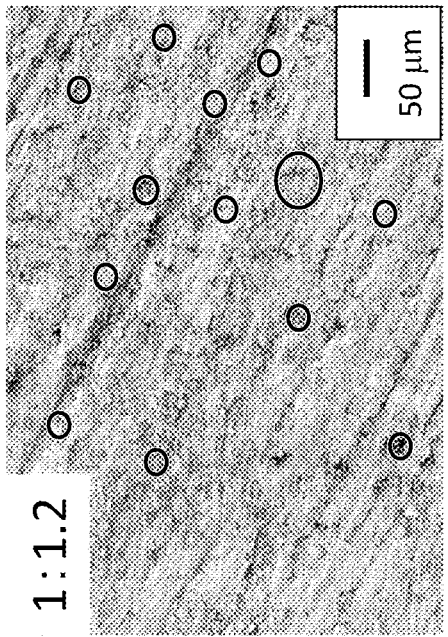

Subsequently, cured bodies of which the mass ratio of an artificial aggregate No. 15 (2 mol % β-TCP/Si which had been subjected to SP treatment and sintered) to a cyanoacrylate adhesive was 1:1, 1:1.1, 1:1.2, and 1:1.3 were polished using waterproof abrasive paper (#1500) to prepare test samples. The obtained test samples were observed using SEM. The results are shown in FIG. 3. In FIG. 3, a region surrounded by a circle (o) indicates a particle of an artificial aggregate.

It was confirmed from FIG. 3 that the artificial aggregates were dispersed and present in each cured body.

(4) Observation with Electron Beam Microanalyzer (Electron Probe Microanalyzer; EPMA)

Figure 4:
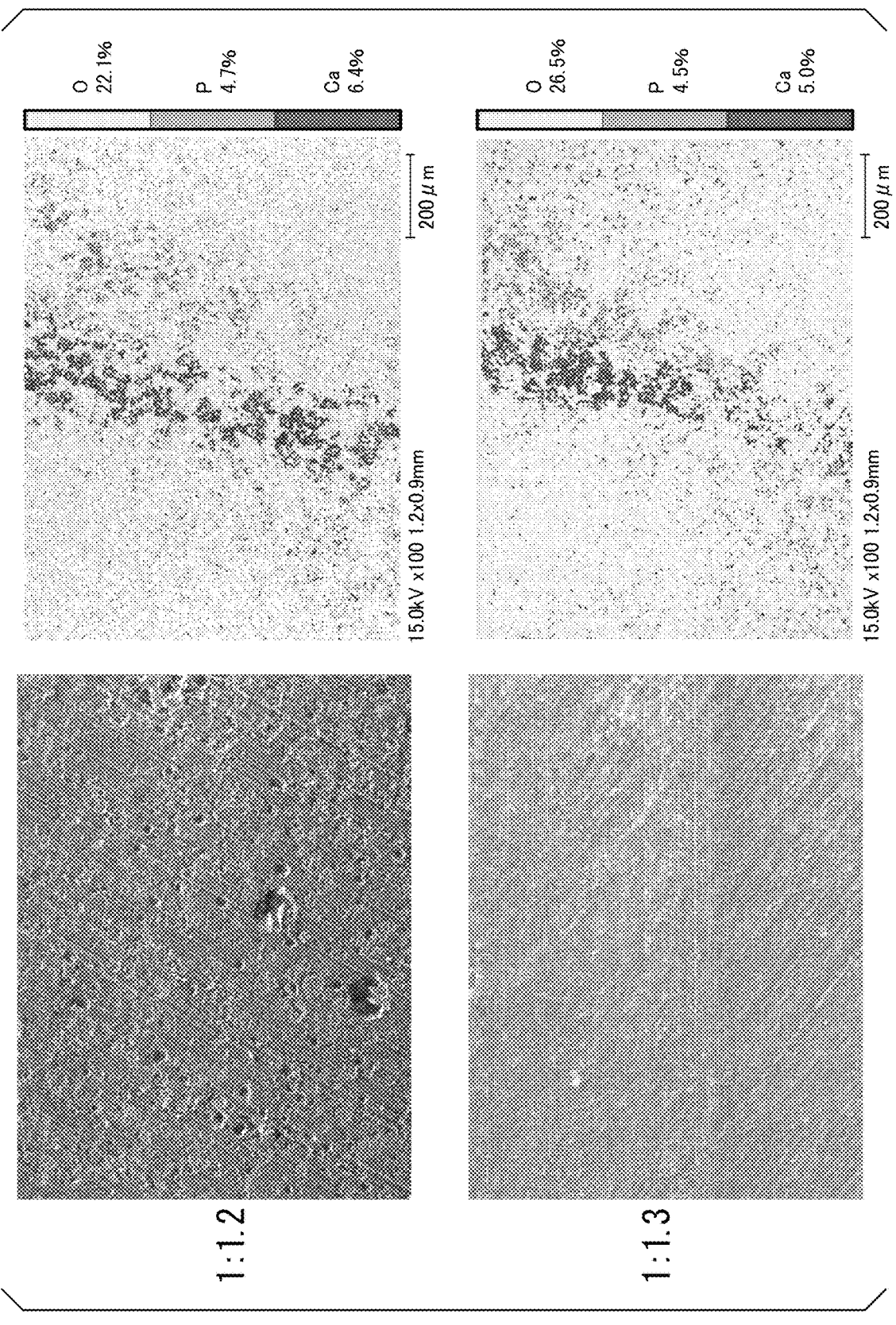
FIG. 4 shows SEM images (left side) and electron beam microanalyzer (electron probe microanalyzer; EPMA) images (right side) of the cured bodies of which the mass ratio of each artificial aggregate (2 mol % β-TCP/Si which had been subjected to SP treatment and sintered) obtained from the kneading test using the syringe of Test Example 1 to a cyanoacrylate adhesive was 1:1.2 and 1:1.3.

Subsequently, cured bodies of which the mass ratio of an artificial aggregate No. 15 (2 mol % β-TCP/Si which had been subjected to SP treatment and sintered) to a cyanoacrylate adhesive was 1:1.2, and 1:1.3 were polished using waterproof abrasive paper (#1500) to prepare test samples. The obtained test samples were observed using an electron beam microanalyzer (electron probe microanalyzer; EPMA). The results are shown in FIG. 4. In FIG. 4, the images on the left are SEM images, and the images on the right are EPMA images.

As shown in FIG. 4, oxygen atoms (O) were widely spread and present. In addition, all of oxygen atoms (O), calcium atoms (Ca), and phosphorus atoms (P) were sparsely spread and present.

Test Example 2 Kneading Test Using Trowel

Figure 5:
FIG. 5 is an image showing a state in which an artificial aggregate is kneaded with a cyanoacrylate adhesive using a trowel in Test Example 2.

Subsequently, tests of mixing with a cyanoacrylate adhesive were performed using all of artificial aggregates Nos. 1 to 21 among the artificial aggregates produced in Production Example 1. Specifically, an artificial aggregate and a cyanoacrylate adhesive (ARON ALPHA (registered trademark) A "Sankyo", Manufacturer and Distributor: TOAGOSEI CO., LTD., Distributor: Daiichi Sankyo, Inc.) were placed in a Teflon (registered trademark) container (100 mL) for stirring shown in FIG. 5, and the artificial aggregate as powder and the cyanoacrylate adhesive were uniformly kneaded using a resin trowel or a resin mixer while avoiding mixing of air bubbles. After kneading, the mixture was continuously kneaded until it had a paste shape. The time from the start of kneading until the mixture had a paste shape and the time from the start of kneading until the mixture was cured were measured. The results are shown in Table 4. The "paste shape" section in Table 4 shows the time after the start of kneading until the mixture had rice cake-like stickiness. In addition, the "curing" section shows the time after the start of kneading until the stickiness of the mixture disappeared and the mixture was cured.

TABLE 4

| No. | Mass ratio (artificial aggregate [g]:cyanoacrylate adhesive [g]) | Paste shape [min] | Curing [min] |
|---|---|---|---|
| 1 | 1.15:1 | To 0.5 | 0.5 To 1 |
| 2 | 1.15:1 | To 3 | To 6 |
| 3 | 1.15:1 | To 3 | To 6 |
| 4 | 1.5:1 | To 0.5 | 0.5 To 1 |
| 5 | 1.5:1 | To 1 | To 3 |
| 6 | 1.5:1 | To 3 | To 10 |
| 7 | 1.56:1 | To 0.5 | 0.5 To 1 |
| 8 | 1.56:1 | To 0.5 | To 3 |
| 9 | 1.56:1 | To 3 | To 20 |
| 10 | 2.7:1 | To 0.5 | 0.5 To 1 |
| 11 | 2.7:1 | To 0.5 | To 2 |
| 12 | 2.7:1 | To 4 | To 30 |
| 13 | 2.7:1 | To 0.5 | 0.5 To 1 |
| 14 | 2.7:1 | To 2 | To 6 |
| 15 | 2.7:1 | To 3 | To 20 |
| 16 | 2:1 | To 0.5 | 0.5 To 1 |
| 17 | 2:1 | To 0.5 | To 2 |
| 18 | 2:1 | To 4 | To 30 |
| 19 | 1.15:1 | To 0.5 | 0.5 To 1 |
| 20 | 1.15:1 | To 1 | To 2 |
| 21 | 1.15:1 | To 1 | To 4 |

From Table 4, in the mixture using each artificial aggregate (No. 3, 6, 9, 12, 15, 18, and 21) sintered at 1,130° C. after SP, the curing time was 4 minutes to 30 minutes. In addition, in the mixtures in which non-SP-treated artificial aggregates (Nos. 2 and 14) sintered at 1,130° C. were used, the curing time was 6 minutes.

From the above, it was confirmed that it is possible to use a mixture of an artificial aggregate having a specific shape and composition, and a cyanoacrylate adhesive at a specific ratio as a bone adhesive having a pot life of 4 minutes to 30 minutes in the kneading using a trowel.

Test Example 3 Rabbit Femur Implantation Test (1) Production of Cured Body (Bone Cement)

Subsequently, a rabbit femur implantation test was performed using a cured body obtained by mixing artificial aggregate No. 12 (1 mol % β-TCP/Si which had been subjected to SP treatment and sintered) among the artificial aggregates produced in Production Example 1 with a cyanoacrylate adhesive.

Specifically, artificial aggregate No. 12 (1 mol % β-TCP/Si which had been subjected to SP treatment and sintered) and a cyanoacrylate adhesive (ARON ALPHA (registered trademark) A "Sankyo", Manufacturer and Distributor: TOAGOSEI CO., LTD., Distributor: Daiichi Sankyo, Inc.) were mixed with each other such that the mass ratio became 61:49 to produce a cured body (bone cement). The obtained cured body (bone cement) had a shape of 4 mm inner diameter×6 mm height, a bulk density of 1.86 g/cm$^3$, and an open porosity of 1.76%.

(2) Implantation into Rabbit Femur

Next, the cured body obtained in (1) was implanted into two places in the rabbit femur.

(3) Observation of Fluorescence Image of Pathological Specimen

A fluorescence image of the implanted portion was observed every week until 18 weeks after the implantation using a fluorescence microscope (Intelligent Microscope BX63 manufactured by Olympus Corporation). In addition, labeling of the bone was performed by administering Calcein (manufactured by Dojindo Molecular Technologies, Inc). Specifically, double labeling was performed by subcutaneously administering calcein to the back of a rabbit, in which the above-described cured body was implanted into the femur, at a dose of 10 mg/0.4 mL per kg of the weight of the rabbit 7 days and 3 days before necropsy to prepare a pathological specimen, in order to analyze tissue kinetics of the bone. An approximate value was used for the weight of the rabbit. Subsequently, a pathological specimen of the implanted portion 18 weeks after the implantation was prepared and a fluorescence image are shown in FIGS. 6A and 6B.

In one implant site, slight bone resorption was recognized from 3 weeks to 12 weeks after the implantation. In addition, in the other implanted portion, slight bone resorption was recognized at 12 weeks after implantation, and mild bone resorption was maintained 12 weeks after the implantation, and the degree of the bone resorption 18 weeks after the implantation was also slight.

Figure 6A:
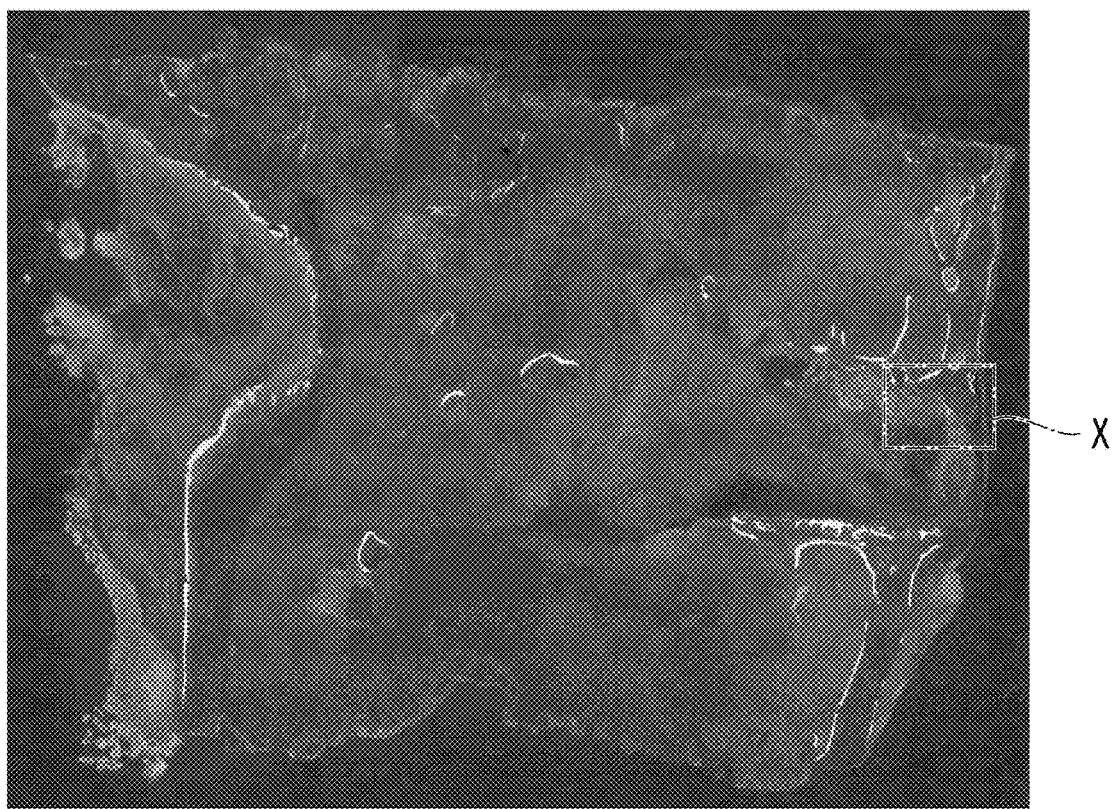
FIG. 6A is a fluorescence image of a pathological specimen prepared 18 weeks after implanting a cured body, which is obtained by mixing an artificial aggregate (1 mol % β-TCP/Si which had been subjected to SP treatment and sintered) in Test Example 3 with a cyanoacrylate adhesive, into the femur of a rabbit.
Figure 6B:
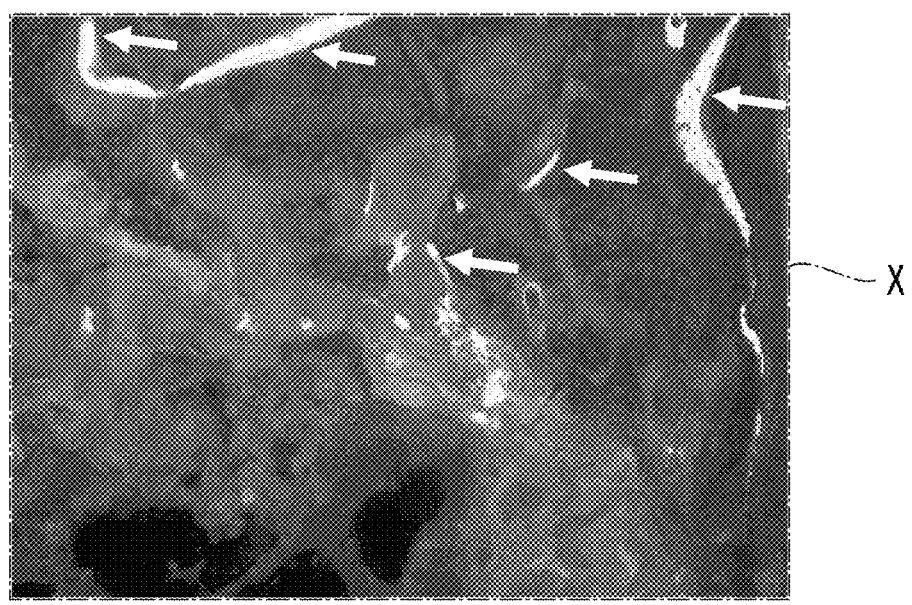
FIG. 6B is an enlarged image of an implanted portion regarding the fluorescence image of the pathological specimen of FIG. 6A in Test Example 3.

In addition, bone regeneration was checked in the implanted portion from FIGS. 6A and 6B.

(4) Observation of Visible Light Image of Pathological Specimen

A pathological specimen of the implanted portion was prepared 18 weeks after the implantation, and a visible light image of the implanted portion was observed using an optical microscope (Intelligent Microscope BX63 manufactured by Olympus Corporation). The results are shown in FIGS. 7A and 7B.

Figure 7A:
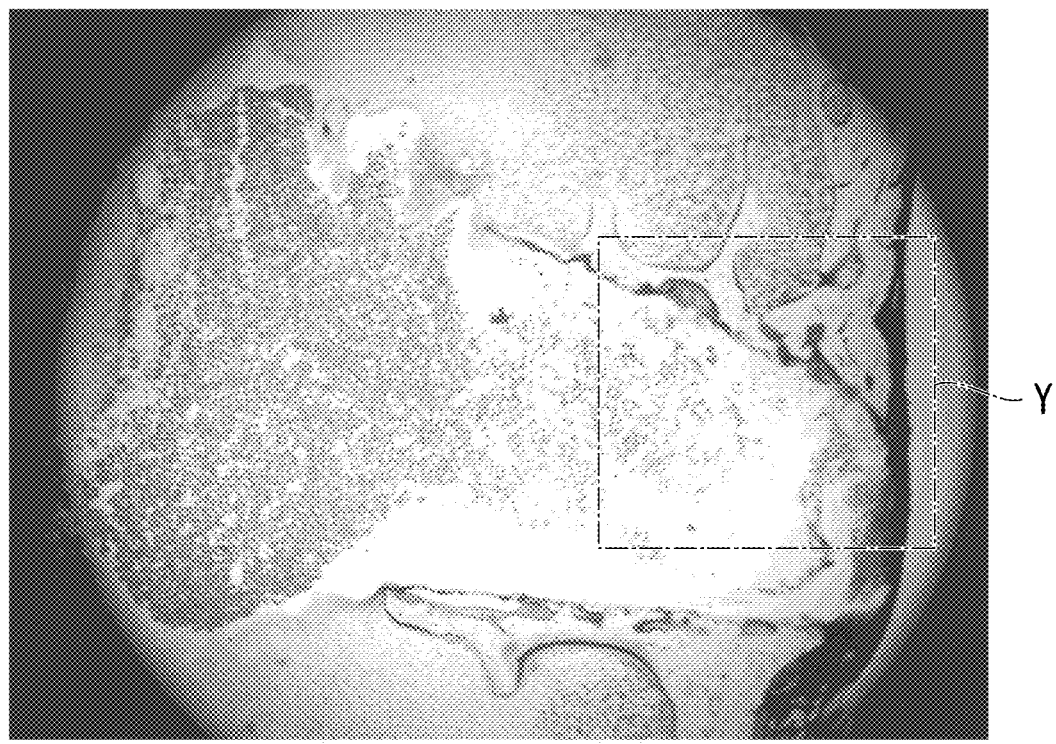
FIG. 7A is a visible light image of the pathological specimen prepared 18 weeks after implanting a cured body, which is obtained by mixing an artificial aggregate (1 mol % β-TCP/Si which had been subjected to SP treatment and sintered) in Test Example 3 with a cyanoacrylate adhesive, into the femur of a rabbit.
Figure 7B:
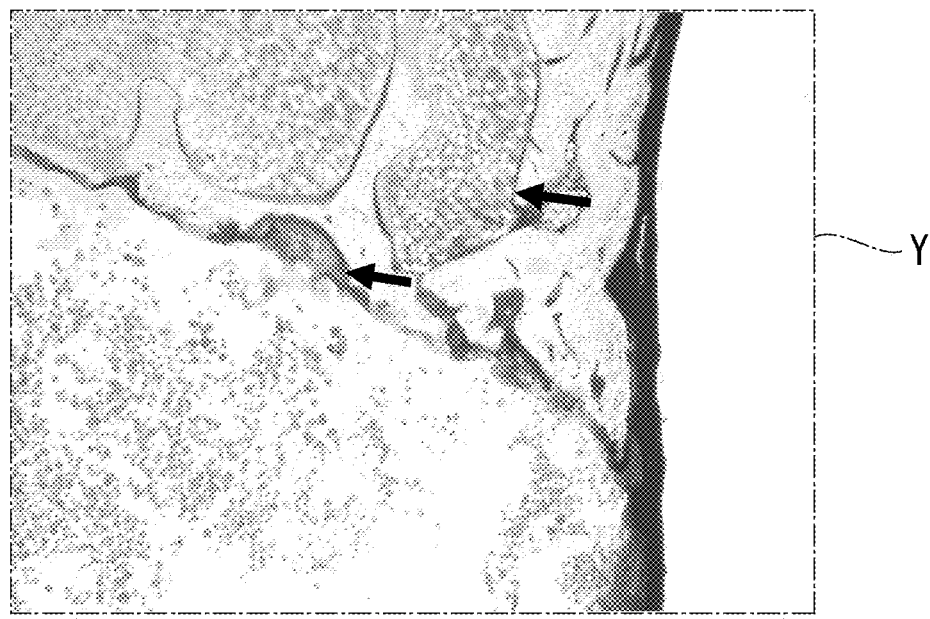
FIG. 7B is an enlarged image of an implanted portion regarding the visible light image of FIG. 7A in Test Example 3.

From FIGS. 7A and 7B, disintegration of the implanted cured body (bone cement) was recognized. In addition, although internal bone formation was not recognized, bone formation was recognized in the periphery of the cortical bone.

Test Example 4 Compressive Strength Test of Cured Body (Bone Cement (1) Production of Cured Body (Bone Cement)

A compressive strength test was performed using a cured body obtained by mixing artificial aggregate No. 18 (3 mol % β-TCP/Si which had been subjected to SP treatment and sintered) among the artificial aggregates produced in Production Example 1 with a cyanoacrylate adhesive (ARON ALPHA (registered trademark) A "Sankyo", Manufacturer and Distributor: TOAGOSEI CO., LTD., Distributor: Daiichi Sankyo, Inc.).

Specifically, 20 g of artificial aggregate No. 18 (3 mol % β-TCP/Si which had been subjected to SP treatment and sintered) and 20 g of a cyanoacrylate adhesive (ARON ALPHA (registered trademark) A "Sankyo", Manufacturer and Distributor: TOAGOSEI CO., LTD., Distributor: Daiichi Sankyo, Inc.) were mixed with each other using a resin trowel for about 8 minutes. Subsequently, a polyethylene terephthalate (PET) test tube (15 mm outer diameter× 100 mm height) was filled with the mixture which was then cured for about 20 minutes. Subsequently, it was confirmed that the mixture was completely cured 5 days after the mixing. Then, the produced cured body (bone cement) in the PET test tube was cut together with the PET test tube using a lathe to obtain a cylindrical cured body (bone cement). The obtained cured body (bone cement) had a shape of about 14 mm diameter×15 mm height. Two cured bodies were produced using the above-described production method.

(2) Compressive Strength Test

Subsequently, the compression breaking load and the compressive elastic force of the two cured bodies obtained as test samples 1 and 2 in (1) were measured using Autograph AG-1 (manufactured by Shimadzu Corporation). Subsequently, the compressive strength was calculated by dividing the obtained compression breaking load by the cross-sectional area of each test sample. In addition, the compression modulus of elasticity was calculated by dividing the compressive elastic force by the cross-sectional area of the test sample. The results are shown in Table 5.

TABLE 5

| | Cured body (bone cement) | Test sample 1 | Test sample 2 |
|---|---|---|---|
| Shape | Diameter (maximum value) [mm] | 14.55 | 14.47 |
| | Diameter (minimum value) [mm] | 13.92 | 13.45 |
| | Cross-sectional area [mm$^2$] | 159 | 152 |
| Compressive strength test | Compression breaking load [kN] | 5.71 | 6.28 |
| | Compressive strength [MPa (N/mm$^2$)] | 35.9 | 41.3 |
| | Compressive elastic force [kN/mm] | 5.70 | 7.00 |
| | Compression modulus of elasticity [GPa (kN/mm$^2$/m)] | 35.8 | 46.1 |

From Table 5, the compressive strength of the obtained cured bodies was about 35 MPa to 45 MPa.

In addition, the compression modulus of elasticity of the obtained cured bodies was about 35 GPa to 50 GPa.

Test Example 5 Three-Point Bending Strength Test of Cured Body (Bone Cement (1) Test Sample A: Production of Cured Body (Bone Cement)

A three-point bending strength test was performed using a cured body obtained by mixing artificial aggregate No. 18 (3 mol % β-TCP/Si which had been subjected to SP treatment and sintered) among the artificial aggregates produced in Production Example 1 with a cyanoacrylate adhesive (ARON ALPHA (registered trademark) A "Sankyo", Manufacturer and Distributor: TOAGOSEI CO., LTD., Distributor: Daiichi Sankyo, Inc.).

Specifically, 10 g of artificial aggregate No. 18 (3 mol % β-TCP/Si which had been subjected to SP treatment and sintered) and 10 g of a cyanoacrylate adhesive (ARON ALPHA (registered trademark) A "Sankyo", Manufacturer and Distributor: TOAGOSEI CO., LTD., Distributor: Daiichi Sankyo, Inc.) were mixed with each other using a resin trowel for about 8 minutes. Subsequently, a silicon test tube (10 mm length×50 mm wide×70 mm height) was filled with the mixture which was then cured for about 20 minutes. Subsequently, it was confirmed that the mixture was completely cured 5 days after the mixing. Then, the produced cured body (bone cement) in the silicon test tube was cut together with the silicon test tube using a lathe to obtain a prism-like cured body (bone cement). The obtained cured body (bone cement) had a shape of about 3 mm length×4 mm wide×30 mm height. Four cured bodies were produced using the above-described production method.

(2) Test Sample B: Production of Cured Body (Bone Cement in Related Art) Made of Only Synthetic Resin A three-point bending strength test was performed using Surgical Simplex (registered trademark) bone cement manufactured by Stryker (registered trademark).

Specifically, 10 g of a liquid monomer (main component: methyl methacrylate) and 20 g of a powdered polymer (main component: methyl methacrylate-styrene copolymer) were mixed with each other for about 5 minutes using a resin trowel. Subsequently, a silicon test tube (10 mm length×50 mm wide×70 mm height) was filled with the mixture which was then cured for about 15 minutes. Subsequently, it was confirmed that the mixture was completely cured 5 days after the mixing. Then, the produced cured body (bone cement) in the silicon test tube was cut together with the silicon test tube using a lathe to obtain a prism-like cured body (bone cement). The obtained cured body (bone cement) had a shape of about 3 mm length×4 mm wide×30 mm height. Four cured bodies were produced using the above-described production method.

(3) Three-Point Bending Strength Test

Subsequently, a three-point bending strength test was performed on the four cured bodies obtained in (1) as test samples A-1, A-2, A-3, and A-4 and the four cured bodies obtained in (2) as test samples B-1, B-2, B-3, and B-4 using Autograph AG-1 (manufactured by Shimadzu Corporation) to measure the bending strength (MPa) and the bending modulus of elasticity (GPa). In the three-point bending strength test, the bending moment (M) was 7.5 [N·mm], the cross section secondary moment (I) was 9.0 [mm$^4$], and M/I was 0.83.

In addition, the bending strength (δ) was calculated using Equation (C). In Equation (C), h represents a longitudinal length [mm] of the test sample, Pmax represents a test force [N], 1 represents a distance [mm] between supporting points (that is, a height of the test sample), and b represents a lateral length [mm] of the test sample.

$$\text{Bending strength } (\delta) = M/I \times h/2 = (3 \times P\max \times l)/(2 \times b \times h2) \quad \text{(C)}$$

In addition, the bending modulus of elasticity (E) was calculated using Equation (C). In Equation (D), Δ represents bending elasticity [N/mm], and l, b and h are the same as those in Equation (C).

$$\text{Bending modulus of elasticity } (E) = (\Delta \times l3)/(4 \times b \times h3) \quad \text{(D)}$$

The results of the test samples A-1, A-2, A-3, and A-4 are shown in Table 6, and the results of test samples B-1, B-2, B-3, and B-4 are shown in Table 7.

TABLE 6

|  |  | Test sample A | | | |
|---|---|---|---|---|---|
|  |  | Test sample A-1 | Test sample A-2 | Test sample A-3 | Test sample A-4 |
| Shape | Mass [g] | 0.599 | 0.636 | 0.667 | 0.690 |
|  | Density [g/cm$^3$] | 1.66 | 1.77 | 1.85 | 1.92 |
| Three-point bending strength test | Maximum load (Pmax) [N] up to breakage | 47 | 45 | 39 | 37 |
|  | Bending strength (δ) [MPa (N/mm$^2$)] | 58.75 | 56.25 | 48.75 | 46.25 |
|  | Bending elasticity (Δ) [N/mm] | 107.5 | 95.0 | 100.0 | 92.5 |
|  | Bending modulus of elasticity (E) [GPa (kN/mm$^2$/m)] | 78.4 | 69.3 | 72.9 | 67.4 |

TABLE 7

|  |  | Test sample B | | | |
|---|---|---|---|---|---|
|  |  | Test sample B-1 | Test sample B-2 | Test sample B-3 | Test sample B-4 |
| Shape | Mass [g] | 0.407 | 0.428 | 0.451 | 0.441 |
|  | Density [g/cm$^3$] | 1.13 | 1.19 | 1.25 | 1.23 |
| Three-point bending strength test | Maximum load (Pmax) [N] up to breakage | 19 | 39 | 35 | 48 |
|  | Bending strength (δ) [MPa (N/mm$^2$)] | 11.60 | 23.81 | 21.37 | 29.30 |
|  | Bending elasticity (Δ) [N/mm] | 43.5 | 44.0 | 50.0 | 86.5 |
|  | Bending modulus of elasticity (E) [GPa (kN/mm$^2$/m)] | 31.7 | 32.1 | 36.5 | 63.1 |

From Tables 6 and 7, the bending strengths of the test samples A-1 to A-4 were about 45 MPa to 60 MPa, which were larger than those of the test samples B-1 to B-4.

In addition, the bending modulus of elasticity of the test samples A-1 to A-4 were about 65 GPa to 80 GPa, which were larger than those of the test samples B-1 to B-4.

From the above, it was confirmed that the bone cement of the present embodiment has higher hardness and elasticity than those of the bone cement in the related art.

INDUSTRIAL APPLICABILITY

The adhesive for hard tissue bonding and the adhesive kit for hard tissue bonding of the present embodiment has a sufficient pot life and excellent biocompatibility. The bone cement of the present embodiment has excellent biocompatibility and is replaced with bone over time. In addition, generation of bone is efficiently encouraged in an in vivo graft of the bone cement of the present embodiment. Accordingly, the adhesive for hard tissue bonding, the adhesive kit for hard tissue bonding, and the bone cement, which is a cured body thereof, of the present embodiment are useful for treating diseases such as osteoarthritis and osteoporosis.

The invention claimed is:

1. An adhesive for hard tissue bonding, the adhesive comprising:
    a cyanoacrylate monomer; and
    beta-tricalcium phosphate,
    wherein the beta-tricalcium phosphate is obtained by molding by a spray-drying granulation method and then calcinating under the conditions of a calcination temperature of 900° C. to 1,180° C.,
    an average particle diameter of the beta-tricalcium phosphate is less than or equal to 100 μm,
    the beta-tricalcium phosphate is a spherical particle, and
    in the beta-tricalcium phosphate, a part of a phosphorus position in a crystal is replaced with a silicon ion by dissolution, a part of a calcium position in a crystal is replaced with a magnesium ion by dissolution and some vacancies existing in a crystalline structure are replaced with sodium ions by dissolution.

2. The adhesive for hard tissue bonding according to claim 1, the adhesive further comprising:
    less than or equal to 5 mol % of the silicon ions with respect to all anion positions.

3. The adhesive for hard tissue bonding according to claim 1,
    wherein an average particle diameter of the beta-tricalcium phosphate is less than or equal to 50 μm.

4. The adhesive for hard tissue bonding according to claim 1,
    wherein in the adhesive, the mass ratio of the beta-tricalcium phosphate to cyanoacrylate monomer is 1:1.3 to 3:1.

5. An adhesive kit for hard tissue bonding, comprising:
    a liquid agent containing a cyanoacrylate monomer; and
    a powdery agent containing beta-tricalcium phosphate,
    wherein the beta-tricalcium phosphate is obtained by molding by a spray-drying granulation method and then calcinating under the conditions of a calcination temperature of 900° C. to 1,180° C.,
    an average particle diameter of the beta-tricalcium phosphate is less than or equal to 100 μm,
    the beta-tricalcium phosphate is a spherical particle, and
    in the beta-tricalcium phosphate, a part of a phosphorus position in a crystal is replaced with a silicon ion by dissolution, a part of a calcium position in a crystal is replaced with a magnesium ion by dissolution and some vacancies existing in a crystalline structure are replaced with sodium ions by dissolution.

6. Bone cement, comprising:
    a cyanoacrylate polymer; and
    beta-tricalcium phosphate,
    wherein the beta-tricalcium phosphate is obtained by molding by a spray-drying granulation method and then calcinating under the conditions of a calcination temperature of 900° C. to 1,180° C.,
    an average particle diameter of the beta-tricalcium phosphate is less than or equal to 100 μm,
    the beta-tricalcium phosphate is a spherical particle, and
    in the beta-tricalcium phosphate, a part of a phosphorus position in a crystal is replaced with a silicon ion by dissolution, a part of a calcium position in a crystal is replaced with a magnesium ion by dissolution and some vacancies existing in a crystalline structure are replaced with sodium ions by dissolution.

7. The bone cement according to claim 6,
    wherein in the bone cement, the mass ratio of the beta-tricalcium phosphate to cyanoacrylate monomer is 1:1.3 to 3:1.

* * * * *